United States Patent [19]

Summerlin

[11] Patent Number: 5,237,105
[45] Date of Patent: Aug. 17, 1993

[54] METHOD FOR REMOVING HYDROFORMYLATION CATALYST

[75] Inventor: William H. Summerlin, Baton Rouge, La.

[73] Assignee: Exxon Chemical Patents Inc., Linden, N.J.

[21] Appl. No.: 891,341

[22] Filed: May 29, 1992

[51] Int. Cl.$^5$ .................. C07C 45/50; C07C 45/78
[52] U.S. Cl. ................................ 568/451; 568/492
[58] Field of Search .................. 568/451, 454, 492

[56] References Cited

U.S. PATENT DOCUMENTS

| | | | |
|---|---|---|---|
| 2,744,921 | 5/1956 | Mertzweiller et al. | 260/414 |
| 2,816,933 | 12/1957 | Mertzweiler | 260/638 |
| 3,520,937 | 7/1970 | Moell et al. | 260/604 |
| 3,725,534 | 4/1973 | Reisch | 423/417 |
| 3,868,422 | 2/1975 | Hart et al. | 260/604 HF |
| 3,941,848 | 3/1976 | Kummer et al. | 260/604 HF |
| 4,390,473 | 6/1983 | Cooper | 260/429 R |
| 4,625,067 | 11/1986 | Hanin | 568/451 |
| 5,091,599 | 2/1992 | DeMunck et al. | 568/882 |

FOREIGN PATENT DOCUMENTS

| | | |
|---|---|---|
| 0011842 | 6/1980 | European Pat. Off. . |
| 0391650 | 10/1990 | European Pat. Off. . |
| 1043097 | 11/1963 | United Kingdom ............. 568/451 |

*Primary Examiner*—Werren B. Lone

[57] ABSTRACT

A method for removing cobalt values from the crude product of a cobalt-catalyzed hydroformylation reaction which utilizes the same equipment in two different operating sequences to accommodate olefinic feedstocks having a wide range of carbon numbers. Olefinic feedstocks having a carbon number in the range $C_4$-$C_{14}$, more preferably $C_5$-$C_7$, can be decobalted by the application of an acid-air cobalt demetalling step upstream of the stripping step of a Cobalt Flash hydroformylation catalyst recovery process; whereas $C_7$ to $C_{20}$ olefinic feedstocks, more preferably $C_8$-$C_{14}$, can be decobalted by application of the acid-air cobalt demetalling step downstream of the stripping step.

26 Claims, 2 Drawing Sheets

METHOD FOR REMOVING HYDROFORMYLATION CATALYST

The present invention relates generally to a method of removing dissolved cobalt compounds from the products of a cobalt catalyzed hydroformylation reaction. This method is particularly useful in removing dissolved cobalt from crude products formed from olefinic feedstocks having a carbon number in the range from about $C_4$ to $C_{14}$, preferably from about $C_5$ to $C_7$.

BACKGROUND OF THE INVENTION

Hydroformylation reactions involve the preparation of oxygenated organic compounds by the reaction of carbon monoxide and hydrogen (a.k.a., syn or synthesis gas) with carbon compounds containing olefinic unsaturation. The reaction is performed in the presence of a carbonylation catalyst and results in the formation of a compound, for example an aldehyde, which has one more carbon atom in its molecular structure than the starting olefinic feedstock. By way of example, higher alcohols may be produced in the so-called "oxo" process by hydroformylation of commercial $C_6$-$C_{12}$ olefin fractions to an aldehyde-containing oxonation product, which on hydrogenation yields respective $C_7$-$C_{13}$ saturated alcohols. The crude product of the hydroformylation reaction will contain catalyst, aldehydes, alcohols, unreacted feed, syn gas and by-products.

Before further processing of the crude product is possible, it is necessary to remove the catalyst therefrom. One conventional method of removing cobalt values from such a crude product is to treat the product with an alkali or acid wash technique. See U.S. Pat. No. 3,725,534 (Reisch), which issued on Apr. 3, 1973. However, this approach uses expensive raw materials and incurs problems associated with finally removing essentially all traces of cobalt from the water wash streams before being discharged.

Another conventional method involves the oxidation of the cobalt catalytic species followed by extraction as a cobalt salt in aqueous solution. See U.S. Pat. No. 2,744,921 (Mertzweiller et al.), which issued on May 8, 1956.

U.S. Pat. No. 4,625,067 (Hanin), which issued on Nov. 25, 1986, discloses still another method which involves the contacting of the crude product with a stream of stripping gas to entrain volatile cobalt compounds, characterized in that the contacting is performed in the presence of water and aqueous acid to dissolve those cobalt values not entrained in the gas under the conditions of temperature and pressure employed for the contacting, and the aqueous phase is subsequently separated from the organic hydroformylation reaction product.

Although the stripping method disclosed in the Hanin patent overcomes the disposal and chemical additive costs of the caustic/acidification method of Reisch, it has the disadvantage that when lower carbon number olefins (e.g., $C_7$ and below) are used as the feedstock, unreacted compounds such as olefins and/or paraffins are stripped out together with the volatile cobalt compounds. These olefins and/or paraffins are then absorbed into the olefinic feedstock and recycled to the oxo reactor. This occurs because lower carbon number feedstocks such as heptene have roughly the same volatility as the cobalt specie, thereby causing it to be entrained together with the volatile cobalt and taken out overhead. Light hydrocarbons which are absorbed into the olefinic feedstock rapidly build up within the cobalt recovery system causing an undesirable decrease in net olefin feed rate.

The present inventor has developed a method of recovering cobalt values which does not cause the build up of unreacted light hydrocarbons within the system, thereby avoiding a decrease in the olefin feed rate. This is accomplished by providing a demetalling step prior to the stripping step which produces a substantially cobalt-free organic hydroformylation reaction product and water soluble cobaltous salt aqueous product. The organic hydroformylation reaction product is diverted for further downstream treatment, while the water soluble cobaltous salt aqueous product is concentrated, converted to cobalt carbonyl and stripped of volatile cobalts substantially free of any light hydrocarbons.

With the addition of the acid-air demetalling step and stream re-routing the same equipment can be used for treating a wide range of carbon number feedstocks, reduce chemical consumption and produce lower quantities of wastewater than conventional systems. Moreover, the method according to the present invention is particularly suited for a closed system, i.e., substantially reduced organic acid and alcohol stream make-up is required.

The present invention also provides many additional advantages which shall become apparent as described below.

SUMMARY OF THE INVENTION

A method for removing cobalt values from the crude product of a cobalt-catalyzed hydroformylation reaction formed from an olefinic feedstock having a carbon number in the range $C_4$-$C_{14}$ wherein an acid-air cobalt demetalling step is disposed upstream of the stripping step of a Cobalt Flash hydroformylation catalyst recovery process. The crude product typically containing cobalt compounds in addition to an organic hydroformylation reaction product.

This method comprises the steps of: (a) contacting the crude product with a stream of oxygen-containing gas, an organic acid and water, thereby producing a substantially cobalt-free organic hydroformylation reaction product and a water soluble cobaltous salt aqueous product; (b) separating the substantially cobalt-free crude product from the water soluble cobaltous salt aqueous product; (c) diverting the substantially cobalt-free organic hydroformylation reaction product for further downstream treatment such as distillation or hydrogenation; (d) concentrating the water soluble cobaltous salt aqueous product, thereby producing a concentrated aqueous solution of cobaltous salt and a substantially cobalt-free water containing the organic acid, whereby the concentrated aqueous solution of cobaltous salt is separated from the substantially cobalt-free water containing the organic acid; (e) recycling the substantially cobalt-free water containing the organic acid to step (a); (f) contacting the concentrated aqueous solution of cobaltous salt with an alcohol stream and synthesis gas, and passing this mixture to a preformer reactor where the concentrated aqueous solution of cobaltous salt is converted to a cobalt carbonyl; (g) contacting the cobalt carbonyl with a stream of stripping gas to entrain volatile cobalt compounds in the stripping gas and to generate as bottoms alcohol products and dissolved cobaltous salts, whereby the entrained volatile cobalt compounds are taken out overhead and the alcohol products and dissolved cobaltous salts are taken out as bottoms; (h) separating the alcohol products of step (g) from the dissolved cobaltous salts; (i) recycling the alcohol products from step (h) to step (f); (j) recycling the dissolved cobaltous salts from step (h) to step (a); and (k) contacting the volatile cobalt compounds from step (g) with the olefinic feedstock; whereby the volatile cobalt compounds are absorbed into the olefinic feedstock.

Another method for removing cobalt values from the crude product of a cobalt-catalyzed hydroformylation reaction formed from an olefinic feedstock having a carbon number in the range $C_7$–$C_{20}$, more preferably in the range between about $C_7$–$C_{14}$, wherein an acid-air cobalt demetalling step is disposed downstream of the stripping step of a Cobalt Flash hydroformylation catalyst recovery process.

This method comprises the steps of: (a) contacting the crude product with water and an organic acid; (b) contacting the product of step (a) with a stream of stripping gas to entrain volatile cobalt compounds in the stripping gas, whereby the entrained volatile cobalt compounds are taken out overhead and organic hydroformylation reaction products containing water soluble cobaltous salts dissolved therein are taken out as bottoms; (c) separating the water soluble cobaltous salt of step (b) from the organic hydroformylation reaction products; (d) diverting the organic hydroformylation reaction product of step (c) for further downstream treatment such as distillation or hydrogenation; (e) contacting the water soluble cobaltous salt of step (c) with a stream of oxygen-containing gas, an organic acid and water, thereby producing a water soluble cobaltous salt aqueous product; (f) concentrating the water soluble cobaltous salt aqueous product from step (e), thereby producing a concentrated aqueous solution of cobaltous salt and a substantially cobalt-free water containing the organic acid, whereby the concentrated aqueous solution of cobaltous salt is separated from the substantially cobalt-free water containing the organic acid; (g) recycling the substantially cobalt-free water containing the organic acid to step (b); (h) contacting the concentrated aqueous solution of cobaltous salt with an alcohol stream, an oxonation product and/or a hydrogenation product and synthesis gas, and passing this mixture to a preformer reactor where the concentrated aqueous solution of cobaltous salt is converted to a cobalt carbonyl; (i) recycling the cobalt carbonyl produced in step (h) to step (a); and (j) contacting the volatile cobalt compounds from step (b) with the olefinic feedstock, whereby the volatile cobalt compounds are absorbed into the olefinic feedstock.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
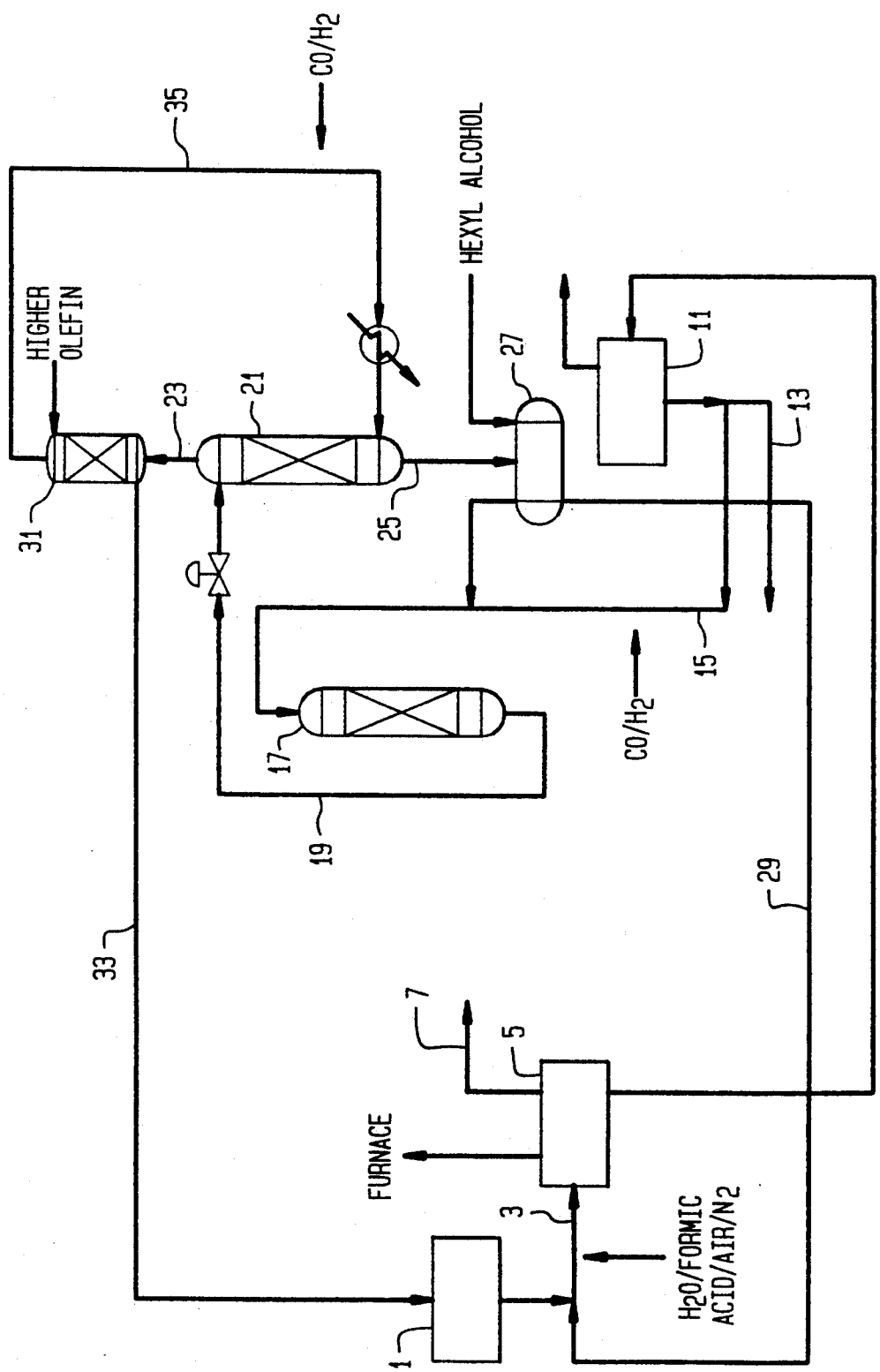
FIG. 1 is a flow diagram of a hydroformylation reaction system embodying the process of the present invention which is capable of removing cobalt values from crude products formed from an olefinic feedstock having a carbon number in the range from about $C_4$ to $C_{14}$, wherein an acid-air cobalt demetalling step is disposed upstream of the stripping step of a Cobalt Flash hydroformylation catalyst recovery process.

Cobalt values can now be successfully removed from crude product of a cobalt-catalyzed hydroformylation reaction from olefinic feedstock without olefinic or paraffin build up during Cobalt Flash catalyst recovery cycles, especially when light hydrocarbons are used as the feedstock. This is accomplished by adding an acid-air cobalt demetalling step to Cobalt Flash catalyst recovery cycles. One particularly suitable Cobalt Flash catalyst recovery cycle is set forth in U.S. Pat. No. 4,625,067, which is incorporated herein by reference. The acid-air cobalt demetalling step is capable of converting cobalt carbonyl to a water soluble cobaltous salt which may be readily separated from organic hydroformylation reaction product such that only the dissolved cobaltous salts after it has been mixed with a recycling alcohol, e.g., hexyl alcohol, and converted to a cobalt carbonyl is passed on to the stripper reactor, thereby avoiding the entrainment of lighter hydrocarbons with the volatile cobalts.

In accordance with the preferred embodiment of the present invention (i.e., the application of an acid-air cobalt demetalling step upstream of the stripping step of a Cobalt Flash hydroformylation catalyst recovery process) air, water, and a organic acid (e.g., formic acid) are mixed with the crude product from an oxo reactor in the acid-air demetalling step described above and allowed to settle. The water stream containing a water soluble cobaltous salt is thereafter separated from the now cobalt-free organic hydroformylation reaction product which is sent directly to hydrogenation thus bypassing the conventional stripping step. The water soluble cobaltous salt is thereafter mixed with the water stream bottoms from the stripper reactor which also contains a cobaltous salt product and these combined streams are fed to an evaporator. The evaporator concentrates the cobaltous salt and generates an overhead stream of cobalt-free water and organic acid which are recycled as wash water and for use in the acid-air demetalling step. The concentrated cobaltous salt stream is mixed with an alcohol stream and fed to a preforming reactor where the cobaltous salt is converted to cobalt carbonyls and then fed to the stripper reactor where the cobalt is stripped overhead using synthesis gas and then absorbed in the feed olefin. The alcohol stream is preferably taken from the bottoms stream of the stripper reactor and recycled back to the preformer reactor.

Accordingly, substantially all of the organic hydroformylation product is separated from the cobaltous salt aqueous product wherein the organic hydroformylation product bypasses the stripper reactor and is sent directly to a hydrogenation or distillation step. As such, the lighter hydrocarbons do not enter the stripper reactor and therefore cannot be entrained together with volatile cobalt. Since the lighter hydrocarbons are not entrained within the volatile cobalt they cannot be absorbed into the olefin feedstock and thus neither build up within the catalyst recovery cycle nor do they effect the net olefin feed rate.

An alternative embodiment of this invention includes the application of an acid-air cobalt demetalling step downstream of the stripping step of a Cobalt Flash hydroformylation catalyst recovery process. This embodiment is particularly useful in decobalting heavier hydrocarbons (i.e., heavier than heptene). In accordance with this embodiment, crude oxonation product bypasses the acid-air demetalling step and, after addition of a organic acid and water, goes directly to the stripper reactor where approximately 70% of the cobalt is stripped overhead as cobalt carbonyl using synthesis gas. The cobalt taken overhead is subsequently absorbed into the feed olefin. The remaining cobalt leaves the stripper reactor as a cobaltous salt via the bottoms stream. This cobaltous salt along with recycled wash water is then be routed to the acid-air demetalling step to remove any trace levels of cobalt carbonyls. The demetalled water stream is then diverted to the evaporator and concentrated. This concentrated cobaltous salt is thereafter mixed with a portion of the cobalt-free organic hydroformylation reaction product from the stripper bottoms stream, or an alcohol product, or recycled hydrogenation product and fed to the preforming reactor. The preformer product is mixed with the oxonation product and fed to the stripper reactor.

Accordingly, cobalt values are removed from the crude oxo product of a cobalt catalyzed hydroformylation reaction by contacting the crude product with a stream of stripping gas to entrain volatile cobalt compounds, characterized in that the contacting is performed in the presence of water and organic acid to dissolve those cobalt values not entrained in the gas under the conditions of temperature and pressure employed for the contacting, and the aqueous phase is subsequently separated from the organic hydroformylation reaction product.

Contrary to upstream use of the acid-air demetalling step, downstream use permits the organic hydroformylation product to enter the stripper reactor wherein volatile cobalt is entrained in the stripping gas and the organics are taken out as bottoms. As discussed above, downstream use of an acid-air demetalling step is only acceptable for treating hydroformylation product prepared from olefins having a carbon number greater than 7. Lighter hydrocarbons would get entrained within the stripping gas and build up within the olefin feed of the catalyst recovery cycle. However, the present inventor has discovered that routing of the water soluble cobaltous salt taken out as bottoms from the stripper reactor to a downstream acid-air demetalling step removes any trace levels of cobalt carbonyls and thus improves the overall performance of the recovery cycle.

The stripping gas which is preferably used in accordance with this invention is synthesis gas (i.e., carbon monoxide and hydrogen mixture). The particular proportions of the two components in the synthesis gas being adjusted to suit the reaction system.

It is preferred that the volume ratio of stripping gas to crude product at the applied conditions be from 20:1 to 250:1, more preferably 50:1 to 125:1. Of course a higher ratio may be used, with good effect, but higher ratios may be detrimental to the economic basis of the process. The limiting lower value of the ratio, it will be appreciated, will be reached when there is insufficient stripping gas flow to achieve the desired degree of volatile cobalt removal. Similarly, any flow rate of stripping gas may be used, sufficient to give the desired entrainment of volatile cobalt. The liquid (i.e., organic plus aqueous) phase is preferably well dispersed to give good contact between the liquids. It is preferred, too, that the stripper reactor include inert solid surfaces or trays to facilitate contact between the liquid and gas phases.

The stripping reactor preferably operates at relatively low pressures, i.e., pressures lower than the decomposition pressure of the cobalt compounds present in the crude hydroformylation reaction product at the temperature conditions employed. More preferably the pressure is below 20.26 bar, most preferably below 10.13 bar, especially for example a low pressure below 7.091 bar such as from 1.013 to 5.065 bar. The temperature employed generally relates to the pressure and is preferably less than or no more than 100° C. or 90° C., more preferably from 60°–100° C., especially 60° to 80°, 85° or 90° C. The temperature in the stripper bottoms is preferably between about 88°–93° C.

In accordance with either mode of operation, the demetalling step is preferably followed by a preformer reactor. The concentrated cobaltous salt is preferably introduced into the cobalt preformer, and the resulting mixture is injected into the crude oxo product downstream of the oxo reactor but upstream of the stripper reactor, or directly into the stripper reactor. Here the stripping gas carries off the volatile cobalt carbonyls (including those newly introduced to the system from the cobalt preformer) and, via absorption into the olefin feed, into the oxo reactor. By such an embodiment only minimal quantities of fresh cobalt need be introduced into the oxo reactor, as make up for an otherwise closed system.

The preformer reaction resulting in the formation of cobalt carbonyl compounds is promoted with a noble metal catalyst, in particular a catalyst selected from the metals of Group IB and VIII of the Periodic Table. Representative examples of useful catalyst material include gold, platinum and palladium. Palladium is the preferred catalyst metal. Preferably, the active catalyst materials are embedded on a solid support such as carbon, coke or alumina. Typically, when a supported catalyst system is used, the active catalyst metal makes up approximately 0.1 to 5.0 weight percent, preferably 0.2 to 2.0 weight percent of the total supported catalyst structure.

The invention may be better understood by reference to the drawings, wherein FIG. 1 illustrates a method for removing cobalt values wherein an acid-air cobalt demetalling step is disposed upstream of the stripping step in a Cobalt Flash process.

FIG. 1 generally depicts a method for removing cobalt values from the crude product of a cobalt-catalyzed hydroformylation reaction formed from an olefinic feedstock having a carbon number in the range $C_4$–$C_{14}$, preferably $C_5$–$C_7$. The crude product typically contains cobalt compounds in addition to an organic hydroformylation reaction product.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 3 where it is contacted with a stream of oxygen-containing gas, an organic acid and water, thereby producing a substantially cobalt-free organic hydroformylation reaction product and a water soluble cobaltous salt aqueous product, to settling drum or demetalling drum 5. In demetalling drum 5 the substantially cobalt-free crude product is separated from the water soluble cobaltous salt aqueous product. The substantially cobalt-free organic hydroformylation reaction product is diverted overhead via conduit 7 for further downstream treatment such as distillation or hydrogenation. The water soluble cobaltous salt aqueous product is carried via conduit 9 to evaporator 11 which concentrates the water soluble cobaltous salt, thereby producing a concentrated aqueous solution of cobaltous salt and a substantially cobalt-free water containing the organic acid, whereby the concentrated aqueous solution of cobaltous salt is separated from the substantially cobalt-free water containing the organic acid. The substantially cobalt-free water containing the organic acid is recycled via conduit 13 to oxo reactor 1. Whereas the concentrated aqueous solution of cobaltous salt is contacted with an alcohol stream and synthesis gas within conduit 15 before this mixture is passed to preformer reactor 17. In preformer reactor 17 the concentrated aqueous solution of cobaltous salt is converted to a cobalt carbonyl under catalytic conditions. The cobalt carbonyl from preformer reactor 17 is carried via conduit 19 to stripper reactor 21 where it is contacted with a stream of stripping gas at a temperature of not greater than 100° C. and at a pressure below 10.13 bar, the pressure being lower than the decomposition pressure of the cobalt compounds at the contacting temperature, to entrain volatile cobalt compounds in the stripping gas and to generate as bottoms alcohol products and dissolved cobaltous salts; whereby the entrained volatile cobalt compounds are taken out overhead via conduit 23 and the alcohol products and dissolved cobaltous salts are taken out as bottoms via conduit 25. The alcohol products are separated from the dissolved cobaltous salts in settling drum 27. The dissolved cobaltous salts are typically in an aqueous phase, e.g., an aqueous salt product, which can be readily separated from the organic phase, i.e., the alcohol products, by gravity settling. The alcohol products from settling drum 27 are preferably recycled to conduit 15 for mixing with the cobaltous salt upstream of preformer reactor 17. The cobaltous salt from settling drum 27 is preferably recycled via conduit 29 to conduit 3 for further demetalling. Finally, the volatile cobalt compounds from conduit 23 are introduced into absorber 31 where they are contacted with olefinic feedstock, whereby the volatile cobalt compounds are absorbed into the olefinic feedstock and recycled to oxo reactor 1 via conduit 33. Reflux from absorber 31 is returned to stripper reactor 21 via reflux conduit 35. Optionally, syn gas may also be fed into stripper reactor 21 via reflux conduit 35.

It is preferable that the oxygen-containing gas introduced into the system at conduit 3 be at least one gas selected from the group consisting of: air, air with nitrogen, carbon dioxide, and mixtures of inert gases with oxygen having an oxygen content in the range of about 2 to about 10%. The amount of oxygen-containing gas used in this catalyst removal process is a function of the cobalt contained in the crude oxo product. For example, if the oxygen-containing gas is a mixture of air and nitrogen, then the amount of air required to convert cobalt carbonyl to $Co^{+2}$ is approximately 130% of theoretical amount, i.e., 1.77 grams of air/gram of cobalt. Nitrogen used to dilute the mixture to about 4 volume % of $O_2$, i.e., 4.11 grams of $N_2$/gram of air. Thus, the air and nitrogen is added to the crude oxo product in an amount of approximately 8.81 grams of gas mixture/gram of cobalt. Since the cobalt concentration in commercial crude oxo products is preferably in the range from about 0.05 to about 0.50 weight %, the oxygen-containing gas is typically added to the crude oxo product in an amount between about 0.45 to about 4.50 weight %. The oxygen-containing gas is then used in an oxygen-containing gas to crude oxo product weight ratio of from about 0.0045:1 to 0.45:1.

The organic acid supplied to conduit 3 for use in the acid-air cobalt demetalling step is typically selected from the group consisting of: formic acid, acetic acid, propionic acid, and other acids having a boiling point approximately the same as water such that appreciable values of acid can be recovered in evaporator 27 for recycling to conduit 3 via conduit 29. It is most preferable that the organic acid be formic acid such that the resultant water soluble cobaltous salt is cobalt formate. The amount of organic acid which is added to the crude oxo product is a function of the amount of cobalt contained within the crude oxo product. Cobalt Flash processes are designed to used 140% of theoretical organic acid to convert cobalt carbonyl to cobalt formate. For example, formic acid may be added to the crude oxo product in an amount of about 2.18 grams of formic acid/gram of cobalt. Thus, if the cobalt concentration in the crude oxo product is in the range between about 0.05 to about 0.50 weight %, then the formic acid is preferably added to the crude oxo product in an amount between about 0.00109 to about 0.0109 grams of formic acid/gram of crude oxo product.

It is preferred that the concentration of the water soluble cobaltous salt aqueous product take place in either a flash unit or evaporator 11 by means of distillation or membrane separation.

Although it is preferable to convert the concentrated aqueous solution of cobaltous salt to a cobalt carbonyl in the presence of a noble metal catalyst disposed within preformer reactor 17, it is optional to convert by contacting of phases at a pressure in the range between about 103 bar (i.e., 1500 psig) to about 310 bar (i.e., 4500 psig) and a temperature in the range between about 100° C. to about 150° C.

It is also optional to subject the substantially cobalt-free organic hydroformylation reaction product diverted from demetalling drum 5 to a water wash treatment in order to remove residual cobalt values remaining therein prior to further downstream treatment such as distillation or hydrogenation. The wash water from this optional treatment can be recycled to conduit 3 to aid in demetalling of the crude oxo product. The water introduced in the acid-air demetalling step via conduit 3 is used in a water to crude product weight ratio of from 0.05:1 to 0.5:1. This ratio is based upon the assumption that 1 wt % cobalt concentration (as cobalt, not cobalt formate) in water is desirable.

Figure 2:
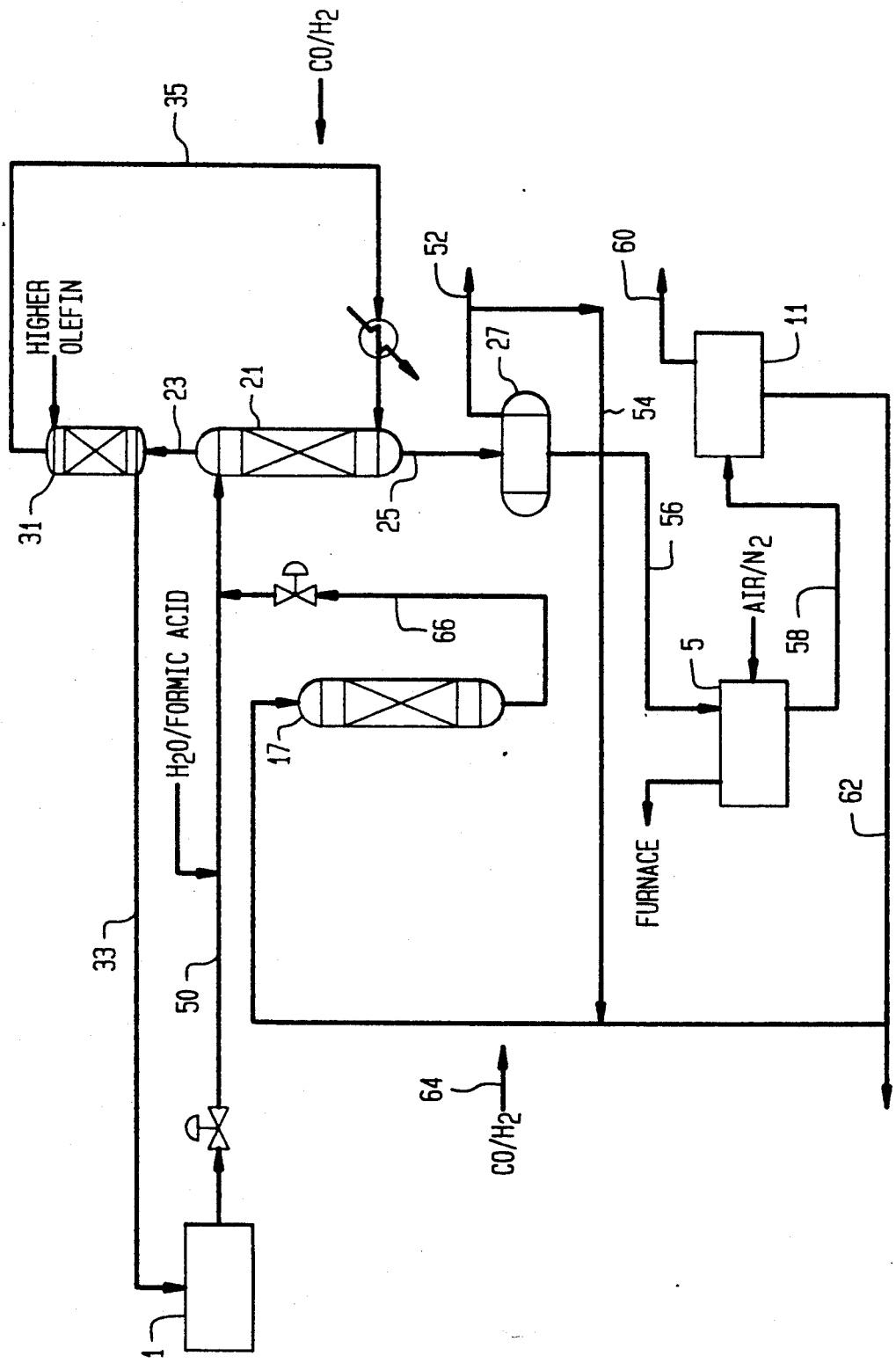
FIG. 2 is a flow diagram of a hydroformylation reaction system embodying another embodiment of the process of the present invention which is capable of removing cobalt values from crude products formed from an olefinic feedstock having a carbon number in the range from about $C_7$ to $C_{14}$, wherein an acid-air cobalt demetalling step is disposed downstream of the stripping step of a Cobalt Flash hydroformylation catalyst recovery process.

FIG. 2 a method for removing cobalt values from the crude product of a cobalt-catalyzed hydroformylation reaction formed from an olefinic feedstock having a carbon number in the range of $C_7$-$C_{14}$, wherein an acid-air cobalt demetalling step is disposed downstream of the stripping step in a Cobalt Flash process.

An olefin feedstock and syn gas are introduced into oxo reactor 1, wherein hydroformylation is conducted under conventional conditions to yield a crude hydroformylation product containing aldehydes, alcohols, by-products and cobalt catalyst compounds. This crude product is carried via conduit 50 where it is contacted with water and an organic acid, such as formic acid. The treated crude product is thereafter contacted with a stream of stripping gas in stripper reactor 21. The stripping typically occurs at a temperature of not greater than 100° C. and at a pressure below 10.13 bar, the pressure being lower than the decomposition pressure of the cobalt compounds at the contacting temperature, to entrain volatile cobalt compounds in the stripping gas, whereby the entrained volatile cobalt compounds are taken out overhead via conduit 23 and organic hydroformylation reaction products containing water soluble cobaltous salts dissolved therein are taken out as bottoms via conduit 25. The water soluble cobaltous salt is then separated from the organic hydroformylation reaction products by means of settling drum 27. The organic hydroformylation reaction product is then carried via conduit 52 for further downstream treatment such as distillation or hydrogenation. Optionally, a portion of the organic hydroformylation product may be diverted from conduit 52 via conduit 54 and recycled to the preformer reactor 17. The water soluble cobaltous salt is carried via conduit 56 to settling drum or demetalling drum 5 where it is contacted with a stream of oxygen-containing gas, an organic acid and water thereby producing a water soluble cobaltous salt aqueous product. The oxygen should be present in an amount such that the organic acid only sees the water. Thereafter, the water soluble cobaltous salt aqueous product is carried via conduit 5B to evaporator 11 which forms a concentrated aqueous solution of cobaltous salt and a substantially cobalt-free water containing the organic acid. The concentrated aqueous solution of cobaltous salt is then separated from the substantially cobalt-free water containing the organic acid, whereby the substantially cobalt-free water containing the organic acid is recycled via conduit 60 to stripper reactor 21, diverted to the optional water wash treatment step, or diverted to hydrogenation. The concentrated aqueous solution of cobaltous salt is carried via conduit 62 either to preformer reactor 17 or recycled to oxo reactor 1. However, prior to being fed to preformer reactor 17, the concentrated cobaltous salt is contacted with an alcohol stream, a cobalt-free organic hydroformylation reaction product, or a hydrogenation product delivered via conduit 54 and syn gas which is delivered via conduit 64. This mixture is then passed on to preformer reactor 17 where the concentrated aqueous solution of cobaltous salt is converted to a cobalt carbonyl. The cobalt carbonyl is then carried via conduits 66 and 50 to stripper reactor 21. Finally, the volatile cobalt compounds which are carried from stripper reactor 21 via conduit 23 are sent to absorber 31 wherein they are absorbed into the olefinic feedstock and returned to oxo reactor 1 via conduit 33.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A method for removing cobalt values form the crude product of a cobalt-catalyzed hydroformylation reaction formed from an olefinic feedstock, said crude product containing cobalt compounds in addition to an organic hydroformylation reaction product, which comprises:

a. contacting said crude product with a stream of oxygen-containing gas, an organic acid selected from the group consisting of: formic acid, acetic acid, propionic acid, and other acids having a boiling point approximately the same as water such that appreciable values of acid can be recovered in step (d), and water thereby producing a substantially cobalt-free organic hydroformylation reaction product and a water soluble cobaltous salt aqueous product;

b. separating said substantially cobalt-free crude product from said water soluble cobaltous salt aqueous product;

c. diverting said substantially cobalt-free organic hydroformylation reaction product for further downstream treatment such as distillation or hydrogenation;

d. concentrating said water soluble cobaltous salt aqueous product thereby producing a concentrated aqueous solution of cobaltous salt and a substantially cobalt-free water containing said organic acid, whereby said concentrated aqueous solution of cobaltous salt is separated from said substantially cobalt-free water containing said organic acid;

e. recycling said substantially cobalt-free water containing said organic acid to step (a);

f. contacting said concentrated aqueous solution of cobaltous salt with an alcohol stream and synthesis gas, and passing this mixture to a preformer reactor where said concentrated aqueous solution of cobaltous salt is converted to a cobalt carbonyl;

g. contacting said cobalt carbonyl with a stream of stripping gas to entrain volatile cobalt compounds in said stripping gas and to generate as bottoms alcohol products and dissolved cobaltous salts, whereby said entrained volatile cobalt compounds are taken out overhead and the alcohol products and dissolved cobaltous salts are taken out as bottoms;

h. separating said alcohol products of step (g) from said dissolved cobaltous salts;

i. recycling said alcohol product from step (h) to step (f);

j. recycling said dissolved cobaltous salts from step (h) to step (a); and k. contacting said volatile cobalt compounds from step (g) with said olefinic feedstock, whereby said volatile cobalt compounds are absorbed into said olefinic feedstock.

2. The method according to claim 1 wherein said oxygen-containing gas is at least one gas selected from the group consisting of: air, air with nitrogen, carbon dioxide, and mixtures of inert gases with oxygen having an oxygen content in the range of about 2 to about 10 weight %.

3. The method according to claim 1 wherein said organic acid is formic acid and the resultant cobaltous salt is cobalt formate.

4. The method according to claim 1 wherein said concentrating step (d) occurs in either a flash unit or evaporator.

5. The method according to claim 1 wherein said concentrated aqueous solution of cobaltous salt is converted to a cobalt carbonyl in the presence of a noble metal catalyst disposed within said preformer reactor.

6. The method according to claim 5 wherein said noble metal catalyst is gold, platinum or palladium.

7. The method according to claim 1 wherein said concentrated aqueous solution of cobaltous salt is converted to a cobalt carbonyl by contacting of phases at a pressure in the range between about 103 bar to about 310 bar and a temperature in the range between about 100° C. to about 150° C.

8. The method according to claim 1 wherein said substantially cobalt-free organic hydroformylation reaction product from step (a) is subjected to a water wash treatment to remove residual cobalt values remaining therein prior to further downstream treatment such as distillation or hydrogenation.

9. The method according to claim 8 wherein wash water from said water wash treatment is recycled to step (a).

10. The method according to claim 1 wherein said organic acid is used in an amount between about 0.00109 to 0.0109 grams of organic acid per gram of said crude product.

11. The method according to claim 1 wherein said oxygen-containing gas is used in a oxygen-containing gas to crude product weight ratio of from about 0.0045:1 to about 0.45:1.

12. The method according to claim 1 wherein said water is used in a water to crude product weight ratio of from 0.05:1 to 0.5:1.

13. The method according to claim 1 wherein said crude product of a cobalt-catalyzed hydroformylation reaction is prepared from olefins having carbon numbers in the range between about $C_4$ to about $C_{14}$.

14. The method according to claim 13 wherein said crude product of a cobalt-catalyzed hydroformylation reaction is prepared from olefins having carbon numbers in the range between about $C_5$ to about $C_7$.

15. A method for removing cobalt values from the crude product of a cobalt-catalyzed hydroformylation reaction formed from an olefinic feedstock, said crude product containing cobalt compounds in addition to an organic hydroformylation reaction product, which comprises:
  a. contacting said crude product with water and an organic acid selected from the group consisting of: formic acid, acetic acid, propionic acid, and other acids having a boiling point approximately the same as water such that appreciable values of acid can be recovered in step (f);
  b. contacting the product of step (a) with a stream of stripping gas to entrain volatile cobalt compounds in said stripping gas; whereby said entrained volatile cobalt compounds are taken out overhead and organic hydroformylation reaction products containing water soluble cobaltous salts dissolved therein are taken out as bottoms;
  c. separating said water soluble cobaltous salt of step (b) from said organic hydroformylation reaction products;
  d. diverting said organic hydroformylation reaction product of step (c) for further downstream treatment such as distillation or hydrogenation;
  e. contacting said water soluble cobaltous salt of step (c) with a stream of oxygen-containing gas, said organic acid and water thereby producing a water soluble cobaltous salt aqueous product;
  f. concentrating the water soluble cobaltous salt aqueous product from step (e) thereby producing a concentrated aqueous solution of cobaltous salt and a substantially cobalt-free water containing said organic acid, whereby said concentrated aqueous solution of cobaltous salt is separated from said substantially cobalt-free water containing said organic acid;
  g. recycling said substantially cobalt-free water containing said organic acid to step (b);
  h. contacting said concentrated aqueous solution of cobaltous salt with synthesis gas and at least one of the following: an alcohol stream and an aldehyde stream, and passing this mixture to a preformer reactor where said concentrated aqueous solution of cobaltous salt is converted to a cobalt carbonyl;
  i. recycling the cobalt carbonyl produced in step (h) to step (a); and
  j. contacting said volatile cobalt compounds from step (b) with said olefinic feedstock, whereby said volatile cobalt compounds are absorbed into said olefinic feedstock.

16. The method according to claim 15 wherein said organic acid is formic acid and the resultant cobaltous salt is cobalt formate.

17. The method according to claim 15 wherein said concentrating step (f) occurs in either a flash unit or evaporator.

18. The method according to claim 15 wherein said concentrated aqueous solution of cobaltous salt is converted to a cobalt carbonyl in the presence of a noble metal catalyst disposed within said preformer reactor.

19. The method according to claim 18 wherein said noble metal catalyst is gold, platinum or palladium.

20. The method according to claim 19 wherein said concentrated aqueous solution of cobaltous salt is converted to a cobalt carbonyl by contacting of phases at a pressure in the range between about 103 bar to about 30 bar and a temperature in the range between about 100° C. to about 150° C.

21. The method according to claims 15 wherein said organic hydroformylation reaction products from step (d) are subjected to a water wash treatment to remove residual cobalt values remaining therein prior to further downstream treatment such as distillation or hydrogenation.

22. The method according to claim 21 wherein wash water from said water wash treatment is recycled to step (a).

23. The method according to claim 15 wherein the crude product of a cobalt-catalyzed hydroformylation reaction is prepared from olefins having carbon numbers in the range between about $C_7$ to about $C_{20}$.

24. The method according to claim 23 wherein the crude product of a cobalt-catalyzed hydroformylation reaction is prepared from olefins having carbon numbers in the range between about $C_8$ to about $C_{14}$.

25. A method for producing higher aldehydes and higher alcohols which comprises:
  hydroformylating an olefinic feedstock with synthesis gas in the presence of a cobalt-containing catalyst to form a crude product containing higher aldehyde, higher alcohol, secondary products and dissolved cobalt catalysts;
  removing said cobalt catalysts from said crude product by the following steps: (a) contacting said crude product with a stream of oxygen-containing gas, an organic acid selected from the group consisting of: formic acid, acetic acid, propionic acid, and other acids having a boiling point approximately the same as water such that appreciable values of acid can be recovered in step (d), and water thereby producing a substantially cobalt-free organic hydroformylation reaction product and a water soluble cobaltous salt aqueous product; (b) separating said substantially cobalt-free crude product from said water soluble cobaltous salt aqueous product; (c) diverting said substantially cobalt-free organic hydroformylation reaction product for further downstream treatment such as distillation or hydrogenation; (d) concentrating the water soluble cobaltous salt aqueous product thereby producing a concentrated aqueous solution of cobaltous salt and a substantially cobalt-free water containing said organic acid, whereby said concentrated aqueous solution of cobaltous salt is separated from said substantially cobalt-free water containing said organic acid; (e) recycling said substantially cobalt-free water containing said organic acid to step (a); (f) contacting said concentrated aqueous solution of cobaltous salt with an alcohol stream and synthesis gas, and passing this mixture to a preformer reactor where said concentrated aqueous solution of cobaltous salt is converted to a cobalt carbonyl; (g) contacting said cobalt carbonyl with a stream of stripping gas to entrain volatile cobalt compounds in said stripping gas and to generate as bottoms alcohol products and dissolved cobaltous salts; whereby said entrained volatile cobalt compounds are taken out overhead and the alcohol products and dissolved cobaltous salts are taken out as bottoms; (h) separating said alcohol products produced in step (g) from said dissolved cobaltous salt; (i) recycling said alcohol for step (h) to step (f); (j) recycling said dissolved cobaltous salt form step (h) to step (a); and (k) contacting said volatile cobalt compounds from step (g) with said olefinic feedstock; whereby said volatile cobalt compounds are absorbed into said olefinic feedstock; and recycling said contacted liquid olefinic feedstock from step (k) to said hydroformylation step.

26. A method for producing higher aldehydes and higher alcohols which comprises:

hydroformylating an olefinic feedstock with synthesis gas in the presence of a cobalt-containing catalyst to form a crude product containing higher aldehyde, higher alcohol, secondary products and dissolved cobalt catalysts;

removing said cobalt catalysts from said crude product by the following steps: (a) contacting said crude product with water and an organic acid; (b) contacting the product of step (a) with a stream of stripping gas to entrain volatile cobalt compounds in said stripping gas; whereby said entrained volatile cobalt compounds are taken out overhead and organic hydroformylation reaction products containing water soluble cobaltous salts dissolved therein are taken out as bottoms; (c) separating said water soluble cobaltous salt of step (b) from said organic hydroformylation reaction products; (d) diverting said organic hydroformylation reaction product of step (c) for further downstream treatment such as distillation or hydrogenation; (e) contacting said water soluble cobaltous salt of step (c) with a stream of oxygen-containing gas, an organic acid selected from the group consisting of: formic acid, acetic acid, propionic acid, and other acids having a boiling point approximately the same as water such that appreciable values of acid can be recovered in step (f), and water thereby producing a water soluble cobaltous salt aqueous product; (f) concentrating the water soluble cobaltous salt aqueous product from step (e) thereby producing a concentrated aqueous solution of cobaltous salt and a substantially cobalt-free water containing said organic acid, whereby said concentrated aqueous solution of cobaltous salt is separated from said substantially cobalt-free water containing said organic acid; (g) recycling said substantially cobalt-free water containing said organic acid to step (b); (h) contacting said concentrated aqueous solution of cobaltous salt with synthesis gas and at least one of the following: an alcohol stream and an aldehyde stream, and passing this mixture to a preformer reactor where said concentrated aqueous solution of cobaltous salt is converted to a cobalt carbonyl; (i) recycling the cobalt carbonyl produced in step (h) to step (a); and (j) contacting said volatile cobalt compounds from step (b) with said olefinic feedstock, whereby said volatile cobalt compounds are absorbed into said olefinic feedstock; and recycling said contacted liquid olefinic feedstock from step (j) to said hydroformylation step.

* * * * *